US006945688B2

(12) United States Patent  
Huyser et al.

(10) Patent No.: US 6,945,688 B2
(45) Date of Patent: Sep. 20, 2005

(54) CONTAINER ASSEMBLY FOR MIXING MATERIALS

(75) Inventors: Richard F. Huyser, Kalamazoo, MI (US); Shea Morrissey, Limerick (IE); David H. Grulke, Battle Creek, MI (US); James F. O'Connell, Portage, MI (US); Christopher Matthew Tague, Portage, MI (US)

(73) Assignee: Stryker Instruments, Kalamazoo, MI (US)

( * ) Notice: Subject to any disclaimer, the term of this patent is extended or adjusted under 35 U.S.C. 154(b) by 463 days.

(21) Appl. No.: 10/043,842

(22) Filed: Jan. 10, 2002

(65) Prior Publication Data

US 2002/0089893 A1 Jul. 11, 2002

Related U.S. Application Data

(60) Provisional application No. 60/261,037, filed on Jan. 10, 2001.

(51) Int. Cl.$^7$ .............................................. B01F 13/06
(52) U.S. Cl. ........................ 366/130; 366/139; 366/347
(58) Field of Search ................................ 366/130, 139, 366/347; 215/341, 344, 354, 356, 296, 363; 220/295, 298, 293

(56) References Cited

U.S. PATENT DOCUMENTS

| | | | | |
|---|---|---|---|---|
| 663,866 A | * | 12/1900 | Copperfield et al. | ........ 220/293 |
| 1,596,367 A | * | 8/1926 | Miller | ........................ 220/293 |
| 2,257,715 A | * | 9/1941 | Hopkins | ..................... 220/293 |
| 2,453,914 A | * | 11/1948 | Hollenback | ................. 366/139 |
| 3,433,385 A | * | 3/1969 | Metivier | ...................... 220/293 |
| 3,494,496 A | * | 2/1970 | Livingstone | ................ 215/344 |
| 3,592,349 A | | 7/1971 | Baugh | |
| 3,704,007 A | * | 11/1972 | Kroeger | ...................... 366/248 |
| 3,741,424 A | | 6/1973 | Landen | |
| 4,182,386 A | | 1/1980 | Alack | |
| 4,185,072 A | | 1/1980 | Puderbaugh et al. | |
| 4,225,247 A | | 9/1980 | Hodson | |
| 4,449,984 A | * | 5/1984 | Cruz | .......................... 604/319 |
| 4,712,699 A | | 12/1987 | Lutz | |
| 4,792,087 A | * | 12/1988 | Russell | ....................... 220/293 |
| 4,856,668 A | | 8/1989 | Pfefferkorn et al. | |
| 4,946,055 A | | 8/1990 | Towns et al. | |
| 4,961,647 A | | 10/1990 | Coutts et al. | |
| 5,135,124 A | * | 8/1992 | Wobser | ...................... 220/296 |
| 5,199,788 A | * | 4/1993 | Stallings | ..................... 366/605 |
| 5,265,956 A | | 11/1993 | Nelson et al. | |
| 5,275,287 A | | 1/1994 | Thompson | |
| 5,344,232 A | | 9/1994 | Nelson et al. | |
| 5,415,474 A | | 5/1995 | Nelson et al. | |
| 5,494,349 A | | 2/1996 | Seddon | |
| 5,549,381 A | | 8/1996 | Hays et al. | |
| 5,558,136 A | | 9/1996 | Orrico | |
| 5,645,347 A | | 7/1997 | Draenert | |
| 5,676,463 A | * | 10/1997 | Larsen | ....................... 366/605 |
| 5,758,797 A | | 6/1998 | Martindale | |
| 6,042,262 A | | 3/2000 | Hajianpour | |
| 6,083,229 A | | 7/2000 | Constantz et al. | |
| 6,089,228 A | | 7/2000 | Smith et al. | |
| 6,338,414 B1 | * | 1/2002 | Schellenbach | .............. 215/344 |

* cited by examiner

Primary Examiner—Tony G. Soohoo
(74) Attorney, Agent, or Firm—Howard & Howard

(57) ABSTRACT

A container assembly for mixing materials having a base defining a mixing chamber for mixing the materials and a cover mounted to the base covering the mixing chamber. A sealing portion depends from the cover and engages an inner wall of the base. The sealing portion is flexible and angled outwardly such that during the engagement of the sealing portion with the inner wall, the sealing portion flexes and conforms to the inner wall to seal the mixing chamber. In addition, a first locking device is disposed on the base and a second locking device is disposed on the cover. A lifting mechanism is disposed on one of the base and cover for automatically lifting the cover relative to the base as the cover is being removed from the base for preventing a discharge of material from the mixing chamber.

59 Claims, 12 Drawing Sheets

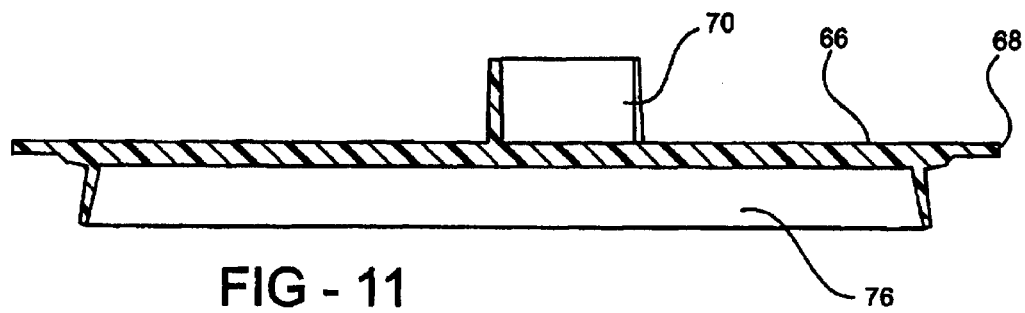
FIG - 11
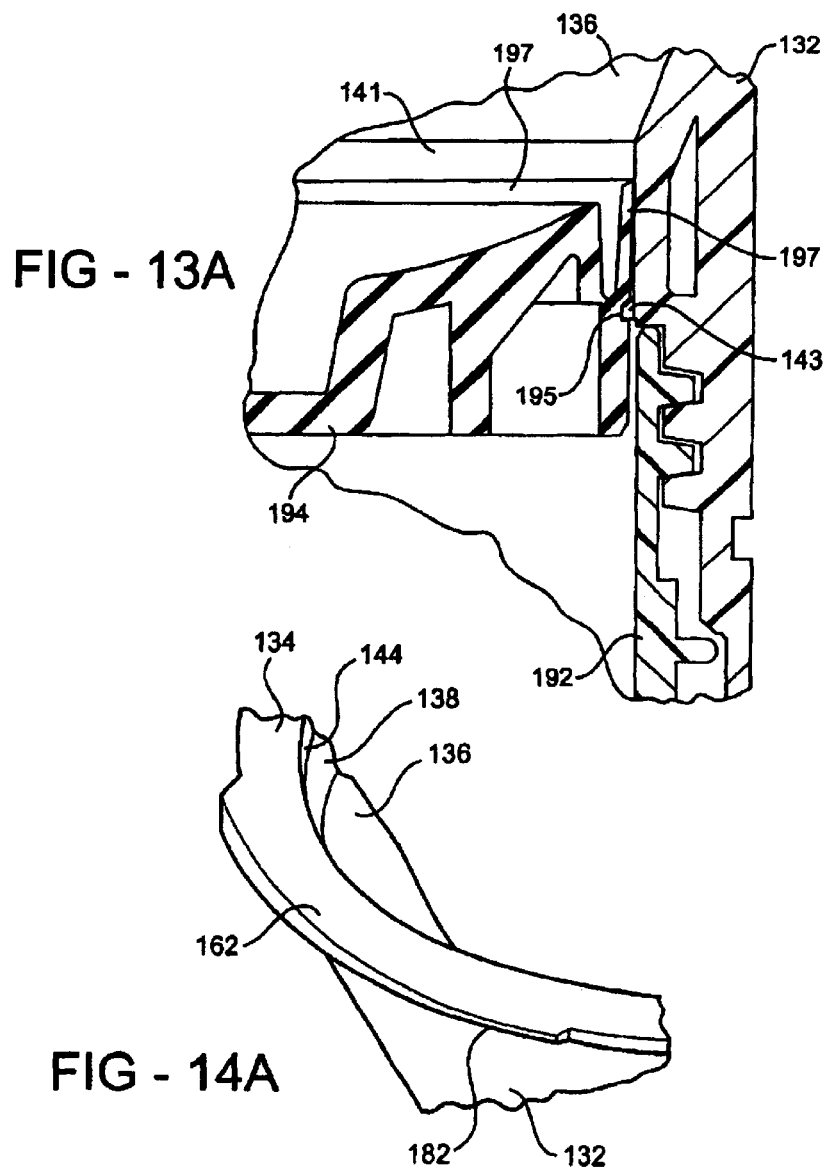
FIG - 13A
FIG - 14A

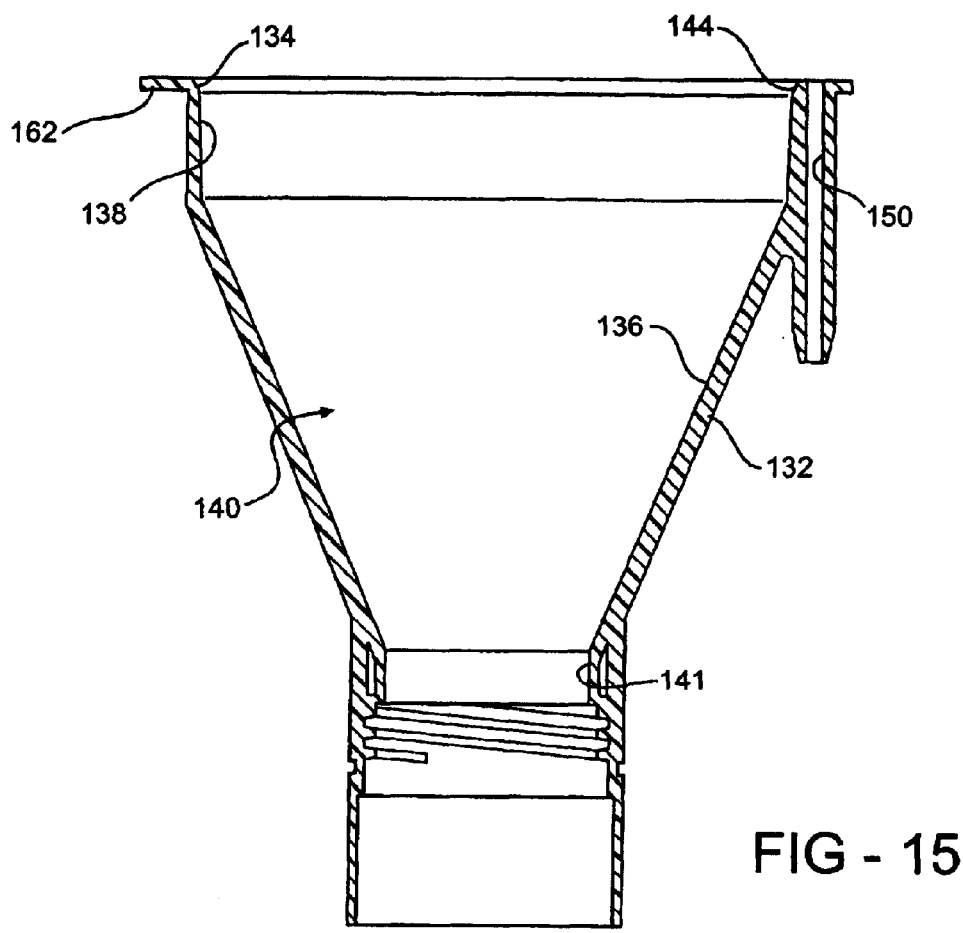
FIG - 15
FIG - 16
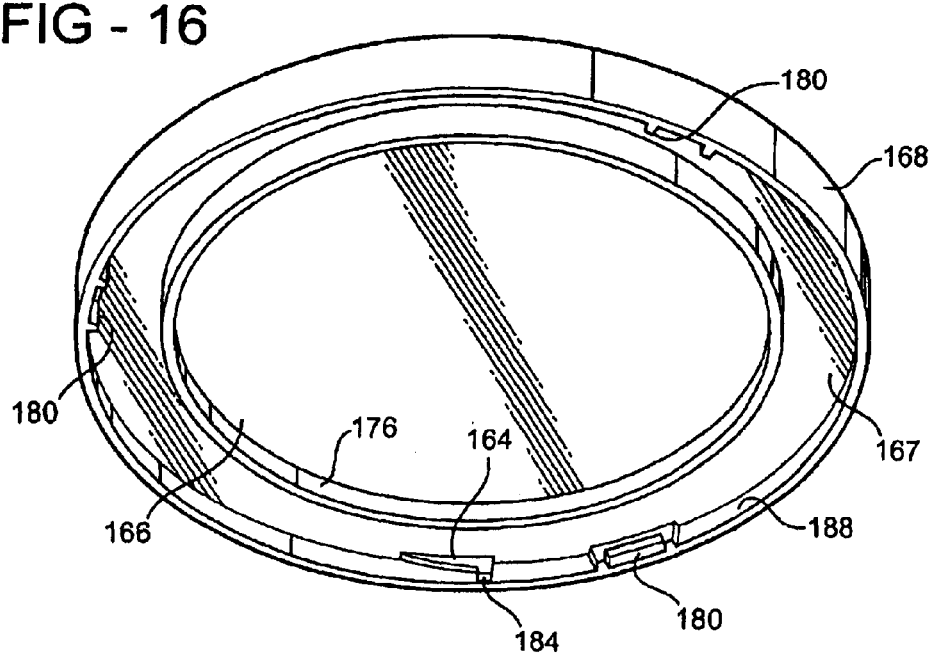

US 6,945,688 B2

CONTAINER ASSEMBLY FOR MIXING MATERIALS

RELATED APPLICATION

The subject patent application claims priority to all the benefits of U.S. Provisional Patent Application Ser. No. 60/261,037, filed on Jan. 10, 2001.

BACKGROUND OF THE INVENTION

1. Field of the Invention

The subject invention relates to a container assembly for mixing materials and in particular for mixing liquid and dry reactants to form bone cement for use in surgical procedures.

2. Description of the Prior Art

It is well known that in many surgical procedures it is necessary to employ a cement or grouting type agent. The type of cement generally used for these procedures is formed of self-curing resins from the blending of a wide variety of liquid monomers or commoners with powdered polymers or copolymers, which forms a viscous mixture. When set, the resulting cements contain ploy (methyacrylic acid esters) as their main ingredient. The solid polymer powder is typically a finely divided air-fluffed powder which can also contain such things as radiopacifiers, antibiotics, plasticizers, crosslinking agents, and compositing reinforcing fibers or beads.

The mixture of the powder and liquid components develops a quick setting material and preparation of the cement usually occurs directly within the operating room just prior to use. The mixing to form the cement typically occurs in a container assembly having a mixing device and a mixing chamber. These type of container assemblies are typically provided in two different forms.

One type of container assembly, which is disclosed in U.S. Pat. No. 4,961,647, includes a mixing bowl having a mixing device. The powder is first placed in the mixing bowl, the liquid component is introduced, and then the mixing device is mounted to the container assembly. After the liquid and powder are mixed to form the cement, the cement can be scooped out of the container assembly with any suitable utensil.

Another type of container assembly, which is disclosed in U.S. Pat. No. 5,265,956, includes a mixing bowl mounted to a cartridge. The mixing bowl also includes a mixing device. The powder is placed into the mixing bowl, the liquid component is introduced, and then the mixing device is mounted to the container assembly. After the liquid and powder are mixed to form the cement, the cement is transmitted into the cartridge. The cartridge is subsequently removed from the container assembly and mounted to an extrusion device.

The container assemblies of the prior art are effective in mixing and delivering the cement. However, there is little development in the prior art regarding the difficulties in introducing the powder to the mixing chamber while ensuring that the powder does not escape from the mixing chamber. As recognized by one skilled in the art, the finely divided air-fluffed powder used in these mixtures has a tendency to escape from the mixing chamber. The discharge of powder is undesirable because of the potential health hazard and the potential to contaminate the operating room. In addition, the escaped powder reduces the amount of cement and can cause an improper mixing ratio between the liquid and the powder, thereby reducing the effectiveness of the powder.

It therefore desirable to pre-pack the mixing chamber with the powder and effectively seal the mixing chamber with a storage cover. It is also desirable to subsequently control the opening of the storage cover from the mixing chamber to reduce or eliminate the discharge of powder.

SUMMARY OF THE INVENTION AND ADVANTAGES

A container assembly for mixing materials comprising a base having a top surface and an inner wall with the inner wall defining an upper surface and a mixing chamber for mixing the materials. The container assembly also comprises a cover having an outer periphery and being selectively mounted to the base covering the mixing chamber and being removable from the base exposing the mixing chamber. A sealing portion depends from the cover and engaging the upper surface of the inner wall when the cover is mounted to the base. The sealing portion is at least partially flexible and angled outwardly toward the outer periphery such that during the engagement of the sealing portion with the upper surface, the sealing portion flexes and conforms to the upper surface to seal the mixing chamber.

In addition, a first locking device is disposed on the top surface of the base and a second locking device is disposed adjacent the outer periphery of the cover. The first and second locking devices interlock the cover to the base when the cover is mounted to the base and release the cover from the base as the cover is being removed from the base. A lifting mechanism is disposed on at least one of the base and cover for automatically lifting the cover relative to the base as the cover is being removed from the base for preventing a discharge of material from the mixing chamber.

The subject invention therefore provide a container assembly which seals the mixing chamber with cover and subsequently controls the opening of the cover from the mixing chamber to reduce or eliminate the discharge of material.

BRIEF DESCRIPTION OF THE DRAWINGS

Other advantages of the present invention will be readily appreciated as the same becomes better understood by reference to the following detailed description when considered in connection with the accompanying drawings wherein:

FIG. 11 is a side view of the alternative cover of FIG. 10;

FIG. 13A is an enlarged fragmentary view of the container assembly of FIG. 12 further illustrating a piston;

FIG. 14A is an enlarged fragmentary view of the base of FIG. 14;

FIG. 15 is a cross sectional side view of the base of FIG. 12;

FIG. 16 is a perspective view of the underside of the cover of FIG. 12;

DETAILED DESCRIPTION OF THE PREFERRED EMBODIMENT

Figure 1:
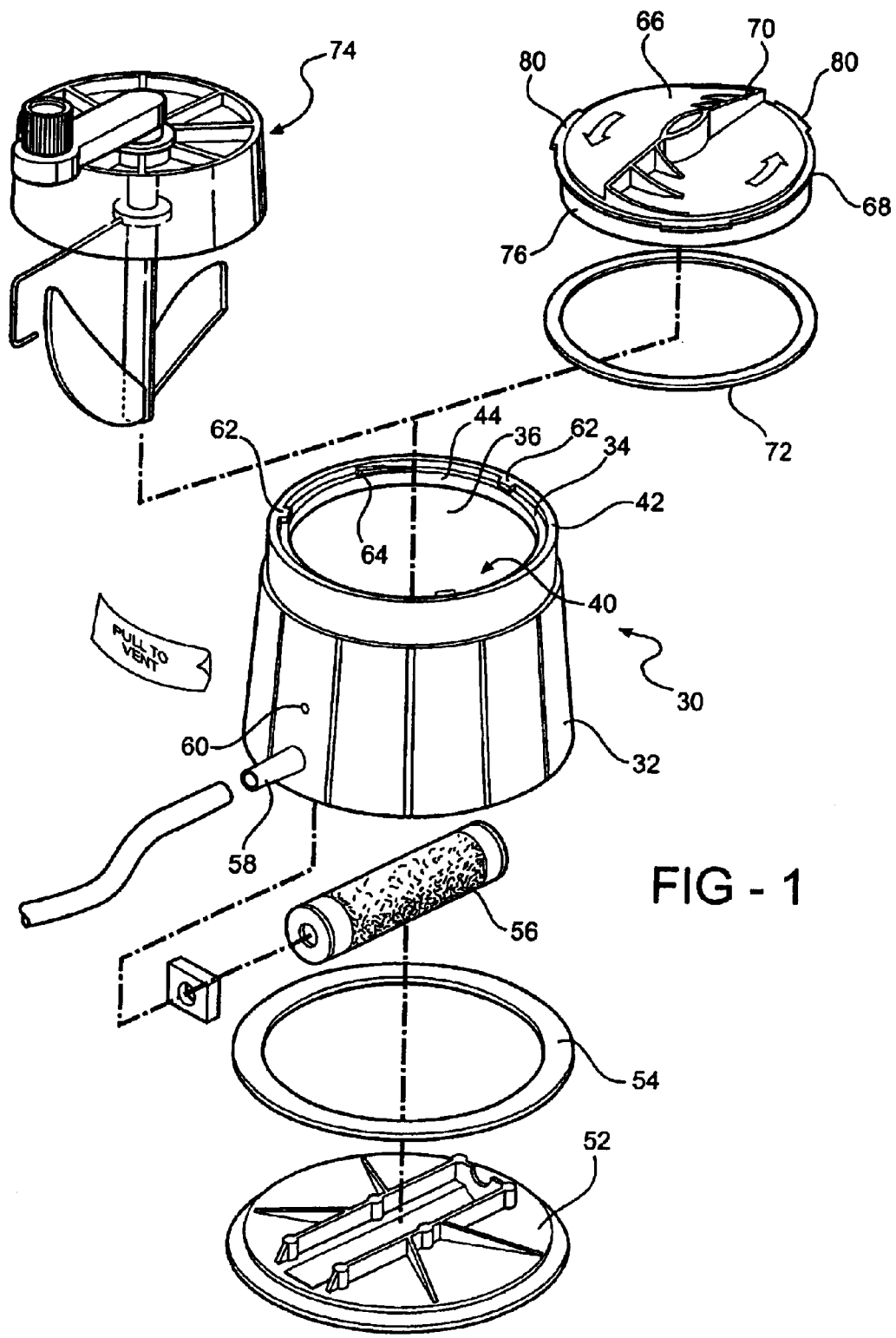
FIG. 1 is a perspective view of a mixing device and a container assembly with the container assembly having a base and a storage cover.

Referring to the Figures, wherein like numerals indicate like or corresponding parts throughout the several views, a container assembly for mixing materials is generally shown at 30 in FIG. 1. As discussed in the background section, container assemblies of this type are typically used to mix a liquid monomer or commoner (not shown) with powdered polymer or copolymer (not shown) to form a bone cement or grouting type agent used in certain surgical procedures. As also discussed above, the solid polymer powder is typically a finely divided air-fluffed powder. The container assembly 30 of the subject invention is pre-packed with the powder such that the container assembly 30 operates as both a storage container and a mixing container. It should be appreciated to those skilled in the art that although the forgoing disclosure only discusses the manufacture of bone cement, that the subject invention can be used to mix other materials without deviating from the scope of the appended claims.

Figure 2:
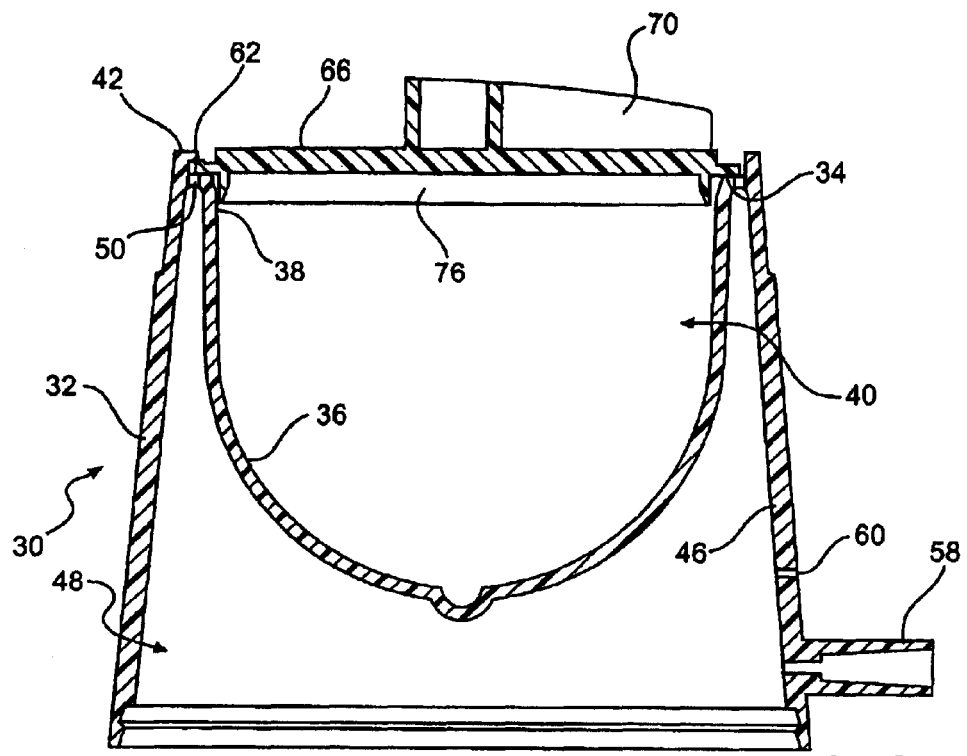
FIG. 2 is a cross sectional side view of the base with the cover mounted thereto.
Figure 3:
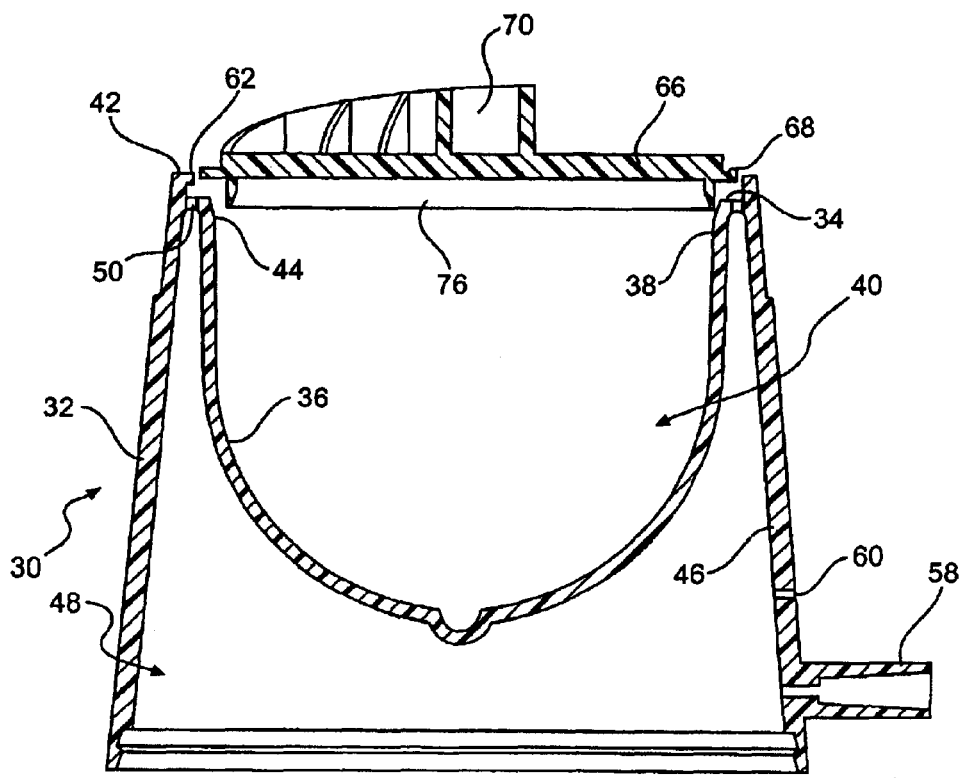
FIG. 3 is a cross sectional side view of the base with the cover being removed therefrom.

Referring also to FIGS. 2 and 3, the container assembly 30 includes a base 32 having a top surface 34 and an inner wall 36. The inner wall 36 defines an upper surface 38 and a mixing chamber 40 for mixing the materials. The mixing chamber 40 is preferably a bowl shaped mixing chamber as is known in the art. Preferably, the top surface 34 extends substantially transverse to the inner wall 36 and the base 32 further includes an outer ridge 42 extending upwardly from the top surface 34 substantially parallel with the upper surface 38 of the inner wall 36. The upper surface 38 of the inner wall 36 also includes a chamfer 44 angled inwardly toward the inner wall 36.

An outer wall 46 surrounds the inner wall 36 to define an evacuation chamber 48 therebetween. The top surface 34 includes at least one aperture 50 for evacuating gases from the mixing chamber 40 into the evacuation chamber 48. As best shown in FIG. 1, the container assembly 30 also includes a bottom plate 52 and seal 54 mounted to an underside of the base 32 to enclose the evacuation chamber 48. A carbon filter 56 is mounted to the bottom plate 52. The carbon filter 56 is in fluid communication with an exhaust port 58 for removing gases from the evacuation chamber 48 during mixing of the liquid and powdered materials. A ventilation hole 60 is also provided within the outer wall 46. The evacuation chamber 48, filter 56, and exhaust port 58 of the base 32 are known features for this type of container assembly 30 and operate in a known manner. As such, these elements will not be discussed in any greater detail.

Figure 4A:
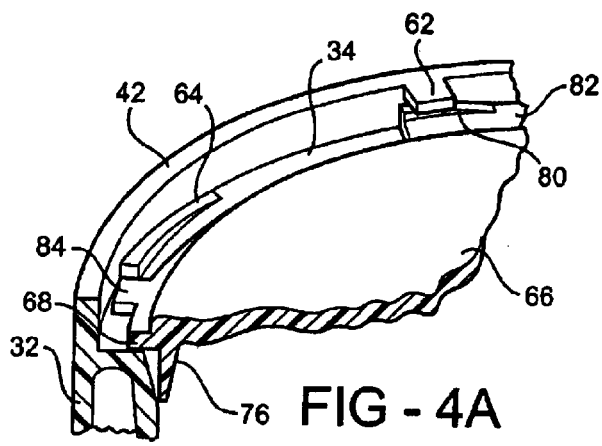
FIG. 4A is an enlarged fragmented view of the base and the cover with the cover in a locked position.
Figure 4B:
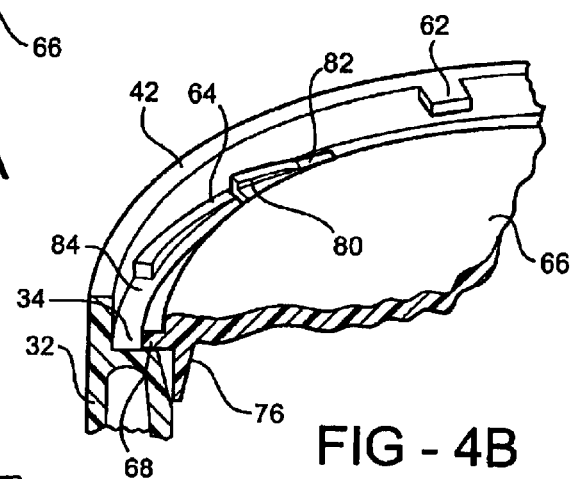
FIG. 4B is an enlarged fragmented view of the base and the cover with the cover in a partially released position.
Figure 4C:
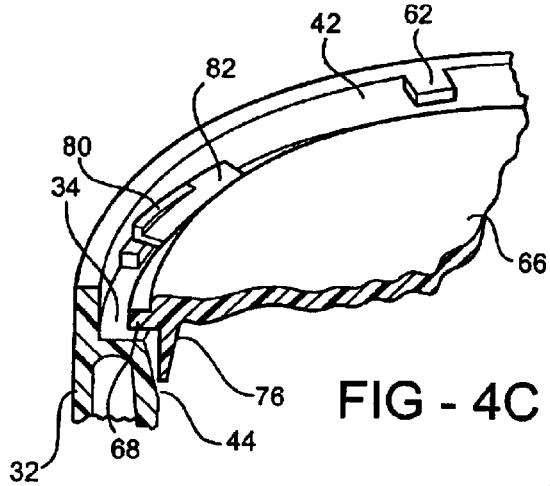
FIG. 4C is an enlarged fragmented view of the base and the cover with the cover in a fully released position.
Figure 5:
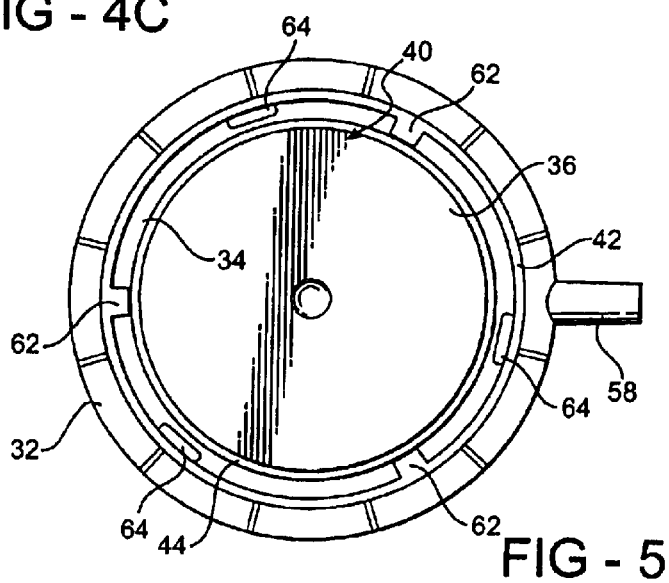
FIG. 5 is a top view of the base.
Figure 6:
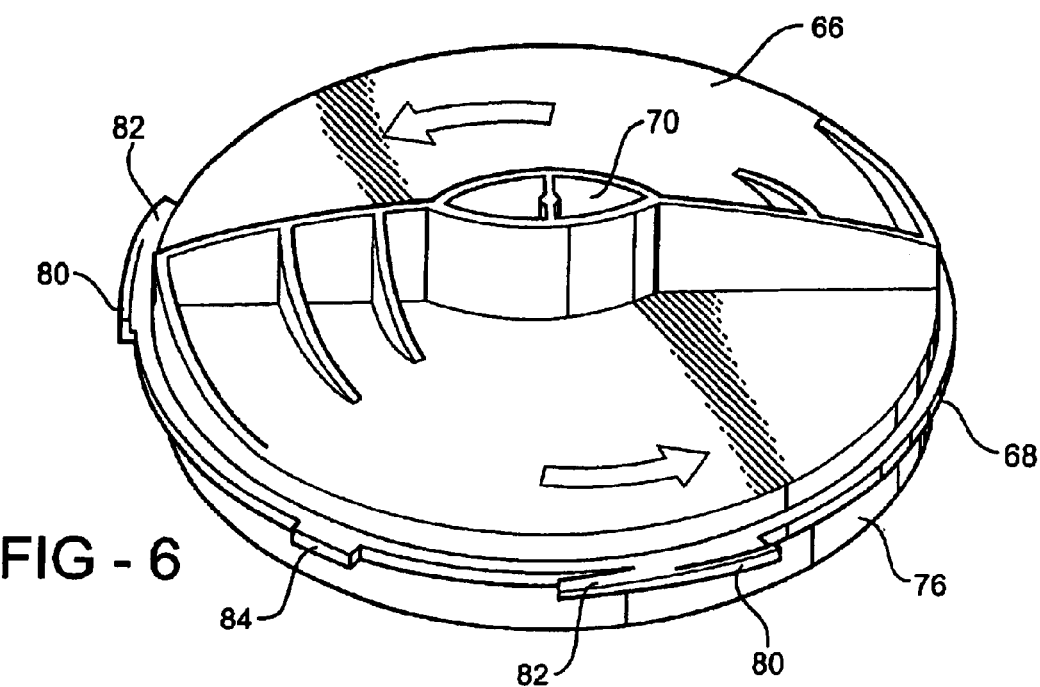
FIG. 6 is a perspective view of the cover.
Figure 7:
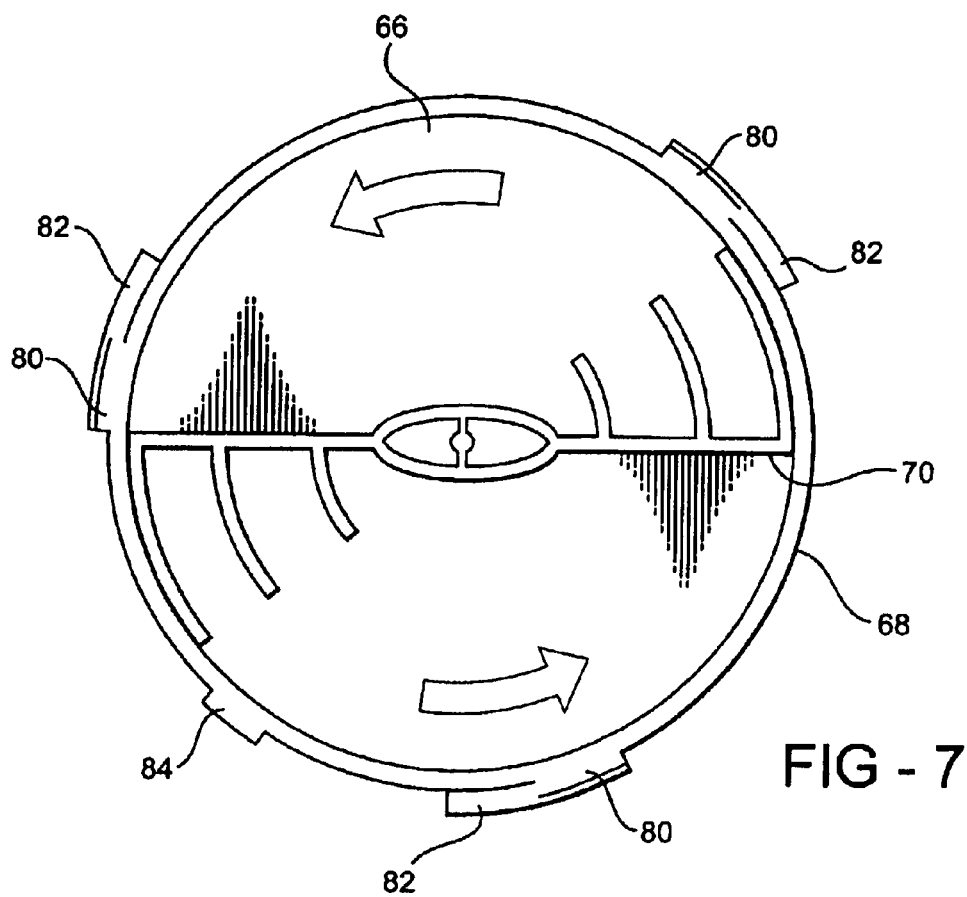
FIG. 7 is a top view of the cover.
Figure 8:
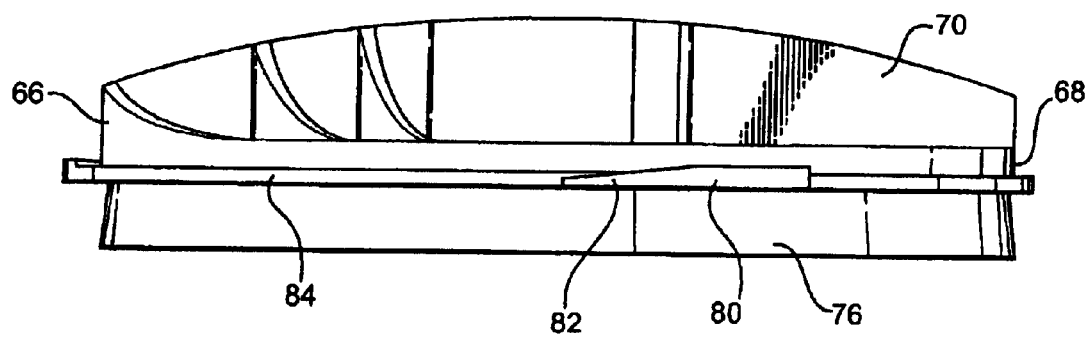
FIG. 8 is a side view of the cover.
Figure 9:
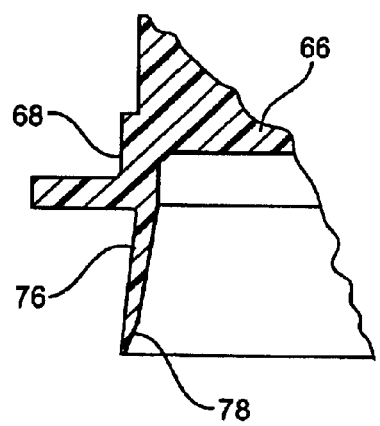
FIG. 9 is an enlarged fragmentary view of the cover.

Referring also to FIGS. 4A through 5, a first locking device 62 is disposed on the top surface 34 of the base 32. In the embodiment of FIGS. 1 through 9, the first locking device 62 is defined as a first tab 62 extending substantially parallel to the top surface 34. The first tab 62 extends from the ridge 42 toward the inner wall 36.

A lifting mechanism 64 is also disposed on the base 32. As illustrated, the lifting mechanism 64 is defined as an angled step 64. Preferably there are three equally spaced first tabs 62 and three equally spaced angled steps 64. Even more preferably, the first tabs 62 and angled steps 64 are spaced equally apart around the perimeter of the top surface 34. The purpose and operation of the first tabs 62 and angled steps 64 is discussed hereinbelow.

As shown in FIGS. 1 through 3, and in more detail in FIGS. 4A through 4C and 6 through 9, a cover 66 having an outer periphery 68 is provided and is selectively mounted to the base 32 covering the mixing chamber 40. A handle 70 is disposed on the cover 66 for allowing manipulation of the cover 66 relative to the base 32. In particular, the cover 66 seats upon the top surface 34 of the base 32 with the ridge 42 surrounding the outer periphery 68 of the cover 66 when the cover 66 is mounted to the base 32.

As best shown in FIG. 1, a seal 72, preferably a rubber or foam gasket, is disposed between the cover 66 and the top surface 34 of the base 32 when the cover 66 is mounted to the base 32. The seal 72 assists in sealing the mixing chamber 40 and preventing the escape of material from the mixing chamber 40. The cover 66 may be removed from the base 32 exposing the mixing chamber 40. When the cover 66 is removed, a mixing device 74, also shown in FIG. 1, is typically mounted to the base 32 to mix the materials. Mixing devices of this type are known in the art and as such will not be discussed in greater detail.

As best shown in FIGS. 2 through 4C, 6, 8, and 9, a sealing portion 76 depends from the cover 66 and engages the upper surface 38 of the inner wall 36 when the cover 66 is mounted to the base 32. The sealing portion 76 is at least partially flexible and angled outwardly toward the outer periphery 68 such that during the engagement of the sealing portion 76 with the upper surface 38, the sealing portion 76 flexes and conforms to the upper surface 38 to seal the mixing chamber 40. The flexing of the sealing portion 76 compensates for any manufacturing defects or tolerances in both the cover 66 and the base 32. Hence, an adequate seal is provided between the cover 66 and the base 32.

Preferably, the sealing portion 76 is spaced inwardly from the outer periphery 68. In addition, the sealing portion 76 is preferably angled outwardly toward the outer periphery 68 from 0.5 to 20 degrees. More preferably, the sealing portion 76 is angled outwardly toward the outer periphery 68 from 2 to 10 degrees, and most preferably, the sealing portion 76 is angled outwardly toward the outer periphery 68 approximately 6.4 degrees. As appreciated, the particular angle of the sealing portion 76 can vary so long as an adequate seal between the cover 66 and the base 32 is maintained. As illustrated, the sealing portion 76 is defined as an annular wedge 76 having a first end and a distal second end. The first end is mounted to the cover 66 and is thicker than the distal end when viewed in cross section, see FIG. 9, to at least partially provide the flexibility of the sealing portion 76. The distal second end also includes a beveled section 78 to further provide the flexibility of the sealing portion 76. The thicker first end of the annular wedge 76 provides a spring loading function for the sealing portion 76 to encourage biased deformation of the thinner distal second end.

In the preferred embodiment, the sealing portion 76 is integrally formed with the cover 66. Even more preferably, the cover 66 and sealing portion 76 are integrally formed of a polymeric material. It should be appreciated that the cover 66 and sealing portion 76 may be formed of any suitable material.

In the embodiment of FIGS. 1 through 9, a second locking device 80 is disposed on the outer periphery 68 of the cover 66 wherein the first 62 and second 80 locking devices interlock the cover 66 to the base 32 when the cover 66 is mounted to the base 32 and release the cover 66 from the base 32 as the cover 66 is being removed from the base 32. As best shown in FIGS. 4A through 4C and 6 through 8, the second locking device 80 is defined as a second tab 80 extending from the outer periphery 68 of the cover 66 and frictionally engaging the first tab 62 when the cover 66 is interlocked to the base 32. The second tab 80 of the cover 66 includes a tapered portion 82 which assists in the mounting and removal of the cover 66 to the base 32. The second tab 80 also engages the lifting mechanism 64, or angled step 64, of the base 32 when the cover 66 is being removed from the base 32, see FIG. 4C. The engagement of the second tab 80 with the angled step 64 provides a controlled lifting feature of the cover 66 relative to the base 32 during removal of the cover 66 from the base 32.

A stop mechanism 84 is disposed on the cover 66 to limit a rotatable movement of the cover 66 relative to the base 32. In the embodiment of FIGS. 1 through 9, the stop mechanism 84 is defined as a stop tab 84 extending from the cover 66 whereby the stop tab 84 selectively engages the first tab 62 of the base 32 during a rotation of the cover 66 relative to the base 32.

The operation of the container assembly 30 of FIGS. 1–9 is now discussed in greater detail. During installation of the cover 66 to the base 32, the annular wedge 76 of the cover 66 engages the chamfer 44 on the upper surface 38 of the inner wall 36 and flexes or otherwise deforms to conform to the configuration of the upper surface 38. Hence, the chamfer 44 guides the distal second end of the annular wedge 76 into the mixing chamber 40 as the cover 66 is mounted to the base 32. The flexing of the annular wedge 76 continues until the second tab 80 and stop tab 84 engage the top surface 34 of the base 32. A portion of the outer periphery 68 of the cover 66 also engages the top surface 34. In addition, the seal 72, if used, is wedged between the outer periphery 68 of the cover 66 and the top surface 34 of the base 32. In this position, the annular wedge 76 of the cover 66 is biased and sealed against the chamfer 44 of the base 32. The cover 66 is then rotated clockwise relative to the base 32 which positions the tapered portions 82 of the second tabs 80 under the first tabs 62 of the base 32. The second tabs 80 then engage the first tabs 62 which completely close the cover 66 onto the base 32. The clockwise rotation continues until the stop tab 84 engages one of the angled steps 64, see FIG. 4A. The cover 66 is now interlocked and sealed to the base 32 which prevents the powder from escaping from the mixing chamber 40.

During removal of the cover 66, the cover 66 is initially interlocked with the base 32 as shown in FIG. 4A. A user then grasps the handle 70 and rotates the cover 66 counter-clockwise. The second tabs 80 will disengage from under the first tabs 62 and the stop tab 84 will rotate away from the adjacent angled step 64, see FIG. 4B. The second tabs 80 will then engage the angled steps 64 which automatically lifts the cover 66 relative to the base 32 as the cover 66 is being removed. This controlled lifting of the cover 66 prevents the discharge of material from the mixing chamber 40 by controlling the flexure of the annular wedge 76 against the inner wall 36. The counter-clockwise rotation and lifting of the cover 66 continues until the second tab 80 has reached the top of the associated angled step 64, see FIG. 4C. In this position the annular wedge 76 has returned to the position adjacent the chamfer 44 of the inner wall 36. The annular wedge 76 has little resistance with the inner wall 36 such that the cover 66 can be easily removed from the base 32.

Figure 10:
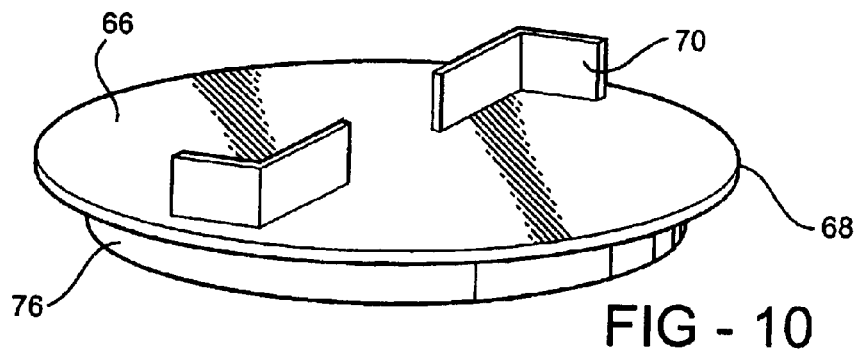
FIG. 10 is a perspective view of an alternative embodiment of the cover.

Referring to FIGS. 10 and 11, an alternative embodiment of the cover 66 is shown. The cover 66 shown in these Figures includes a sealing portion 76 in accordance with the subject invention spaced inwardly from an outer periphery 68. The cover 66 does not include a locking device or a stop mechanism.

Figure 12:
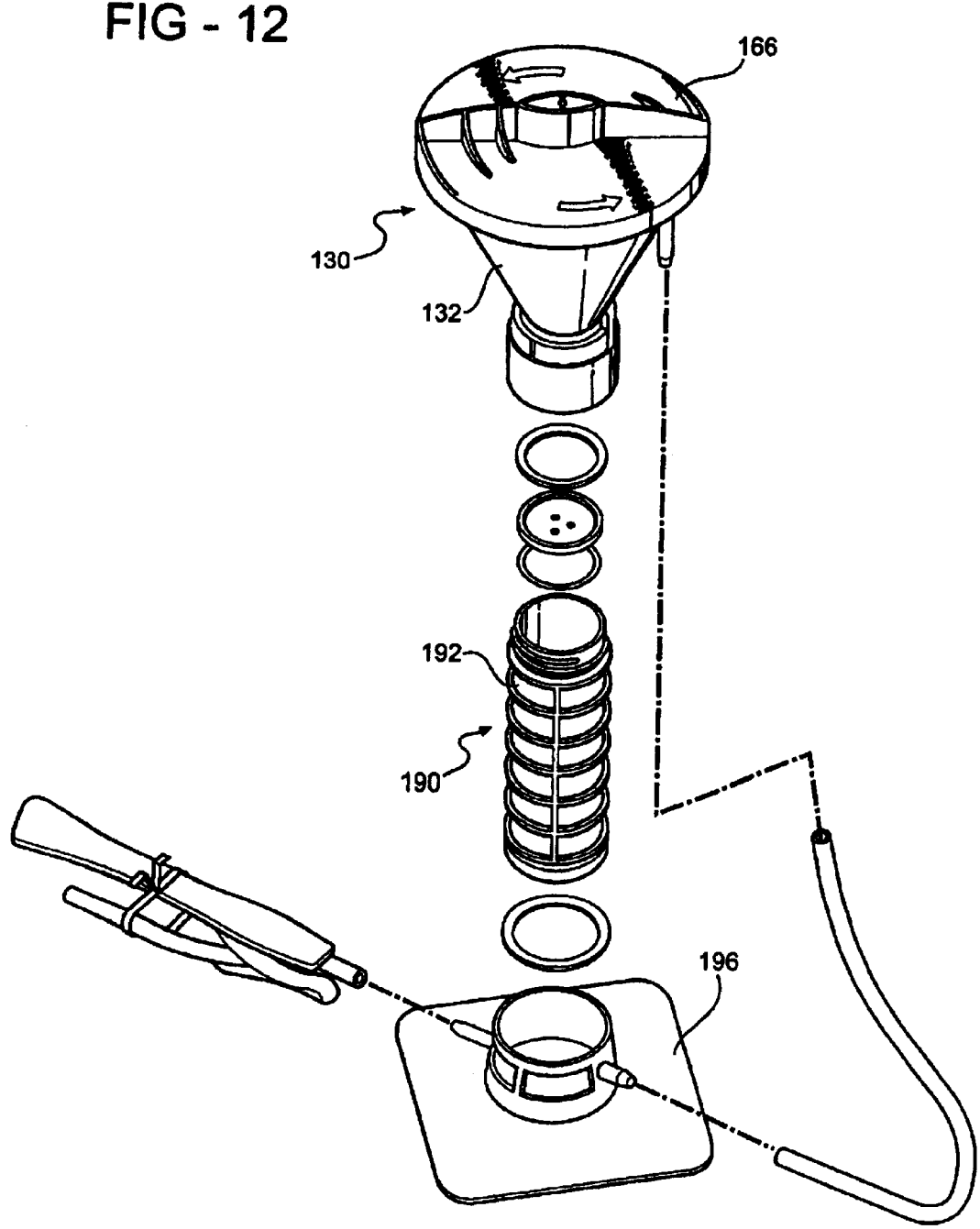
FIG. 12 is a perspective view of a loading apparatus and an alternative container assembly with the container assembly having a base and a cover.
Figure 13:
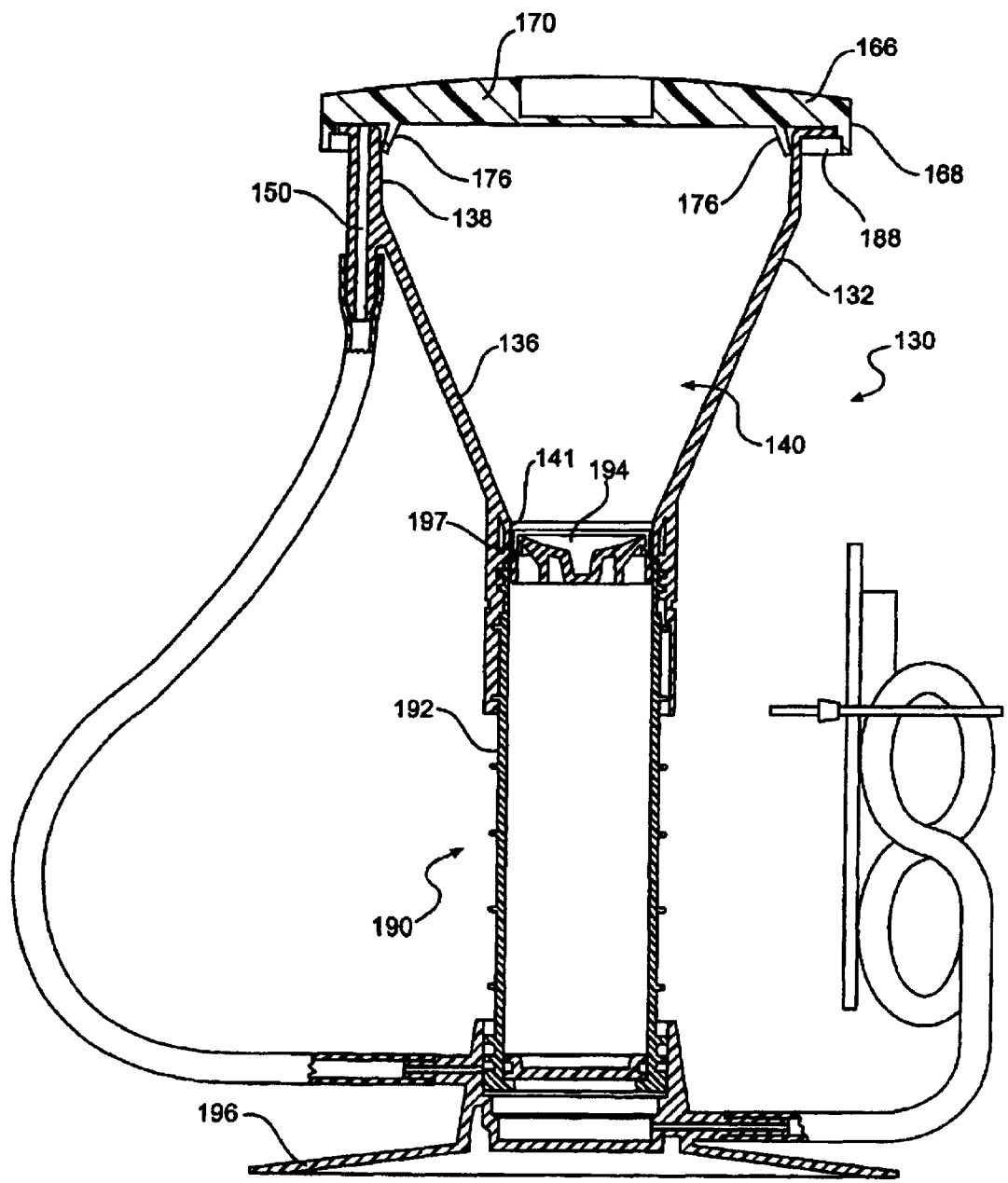
FIG. 13 is a cross sectional side view of the loading apparatus and container assembly of FIG. 12.

Turning to FIGS. 12 through 19B, an alternative embodiment of the subject invention is shown wherein like numerals increased by one hundred indicate like or corresponding parts throughout the several views. Referring to FIGS. 12 and 13, a container assembly for mixing materials is generally shown at 130 and a loading apparatus is generally shown at 190. As with the primary embodiment outlined above, the container assembly 130 of the subject invention is pre-packed with the powder such that the container assembly 130 operates as both a storage container and a mixing container.

The loading apparatus 190 includes a cartridge 192 located below the container assembly 130 for receiving mixed bone cement therefrom. The cartridge 192 is mounted to a vacuum shroud 196. Once filled, the cartridge 192 can be removed from both the vacuum shroud 196 and container assembly 130, and be subsequently mounted to an extrusion device (not shown). Loading apparatuses of this type are well known in the art and will not be discussed in any greater detail.

Figure 14:
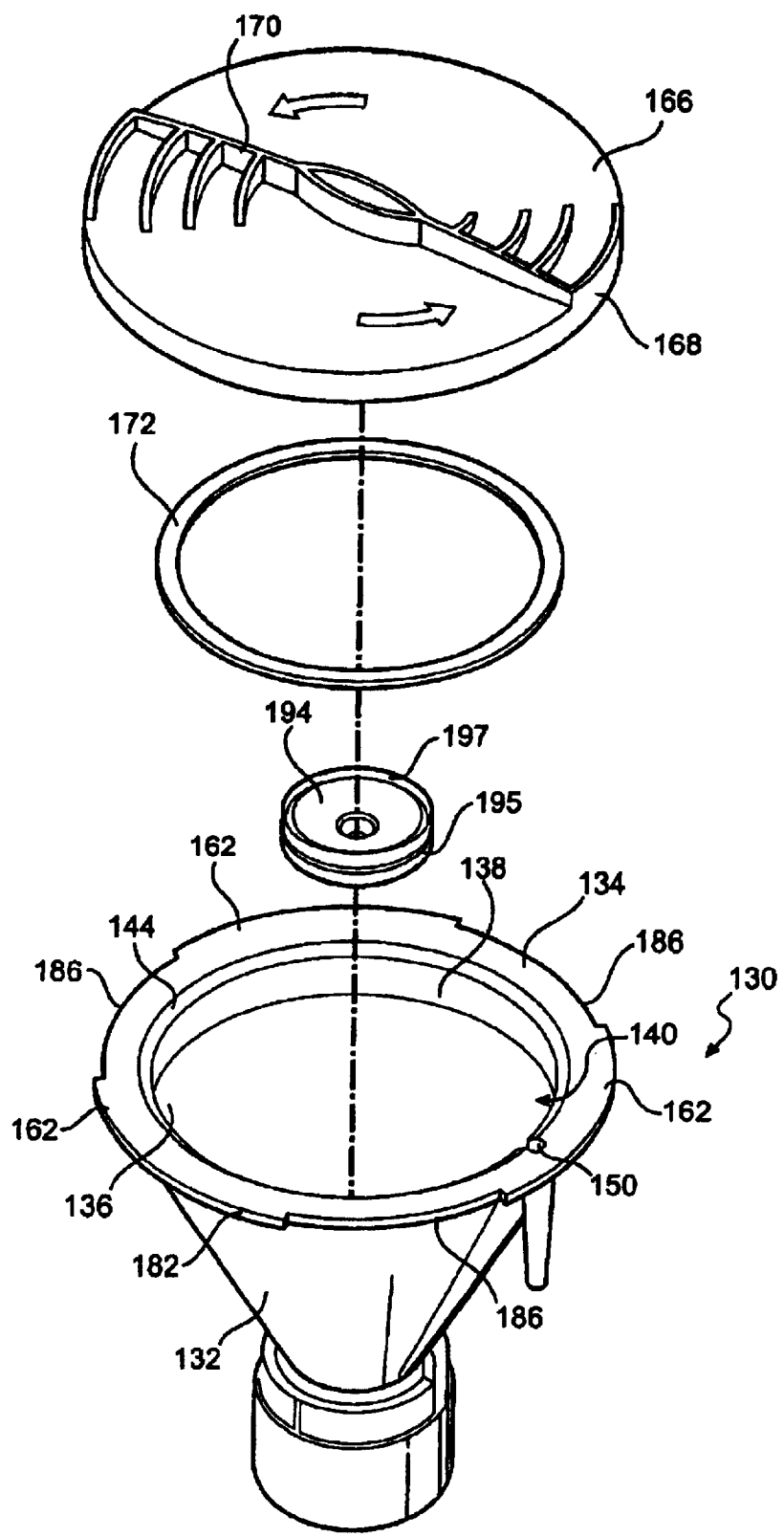
FIG. 14 is a perspective view of the container assembly of FIG. 12.

Referring also to FIGS. 14 and 15, the container assembly 130 includes a base 132 having a top surface 134 and an inner wall 136. The inner wall 136 defines an upper surface 138 and a mixing chamber 140 for mixing the materials. The mixing chamber 140 has a frusto-conical funnel-type shape terminating at a bottom opening 141. The upper surface 138 of the inner wall 136 includes a chamfer 144 angled inwardly toward the inner wall 136.

The top surface 134 extends substantially transverse to the inner wall 136 with a first locking device 162 being disposed on the top surface 134 of the base 132. In the embodiment of FIGS. 12 through 19B, the first locking device 162 is defined as a first tab 162 extending outwardly from the top surface 134 wherein the first tab 162 of the base 132 includes a tapered portion 182. The tapered portion 182 is best shown in FIG. 14A. Preferably there are three equally spaced first tabs 162 disposed about the top surface 134 of the base 132 with a notch 186 being formed between each of the first tabs 162. The purpose and operation of the first tabs 162 is discussed hereinbelow. The top surface 134 also includes an aperture 150 for evacuating gases from the mixing chamber 140.

Referring to FIGS. 13, 13A, and 14, a piston 194 is disposed between the bottom opening 141 of the base 132 and the cartridge 192. The bottom opening 141 includes an annular rib 143 and the piston 194 includes an annular notch 195 for engaging the rib 143 to retain the piston 194 in position. The piston 194 also includes a annular sealing ring 197 which engages the bottom opening 141 to seal the bottom opening 141 and prevent the escape of powder from the mixing chamber 140. The sealing ring 197 is at least partially flexible and angled outwardly toward the bottom opening 141 such that the sealing ring 197 flexes and conforms to the bottom opening 141 to seal the bottom opening 141.

As shown in FIGS. 12 through 14, and in more detail in FIGS. 16 through 19B, a cover 166 having an outer periphery 168 is provided and is selectively mounted to the base 132 covering the mixing chamber 140. A handle 170 is disposed on the cover 166 for allowing manipulation of the cover 166 relative to the base 132.

The cover 166 further includes an outer flange 188 substantially encapsulating the top surface 134 of the base 132 when the cover 166 is mounted to the base 132. In particular, the cover 166 seats upon the top surface 134 of the base 132 with the flange 188 surrounding the top surface 134 and first tabs 162. A seal 172, preferably a rubber or foam gasket, is disposed between the cover 166 and the top surface 134 of the base 132 when the cover 166 is mounted to the base 132, see FIG. 14. The seal 172 assists in sealing the mixing chamber 140 and preventing the escape of material from the mixing chamber 140.

A sealing portion 176 depends from the cover 166 and engages the upper surface 138 of the inner wall 136 when the cover 166 is mounted to the base 132. The sealing portion 176 is at least partially flexible and angled outwardly toward the outer periphery 168 such that during the engagement of the sealing portion 176 with the upper surface 138, the sealing portion 176 flexes and conforms to the upper surface 138 to seal the mixing chamber 140.

Preferably, the sealing portion 176 is spaced inwardly from the flange 188. In addition, the sealing portion 176 is preferably angled outwardly toward the outer periphery 168 from 0.5 to 20 degrees. More preferably, the sealing portion 176 is angled outwardly toward the outer periphery 168 from 2 to 10 degrees, and most preferably, the sealing portion 176 is angled outwardly toward the outer periphery 168 at approximately 7.5 degrees. As discussed above with regard to the primary embodiment, the particular angle of the sealing portion 176 can vary so long as an adequate seal between the cover 166 and the base 132 is maintained. The sealing portion 176 is defined as an annular wedge 176 having a first end and a distal second end. The first end is mounted to the cover 166 and is thicker than the distal end when viewed in cross section to at least partially provide the flexibility of the sealing portion 176. The thicker first end of the annular wedge 76 provides a spring loading function for the sealing portion 76 to encourage biased deformation of the thinner distal second end.

In the preferred embodiment, the sealing portion 176 is integrally formed with the cover 166. Even more preferably, the cover 166 and sealing portion 176 are integrally formed of a polymeric material.

Figure 17:
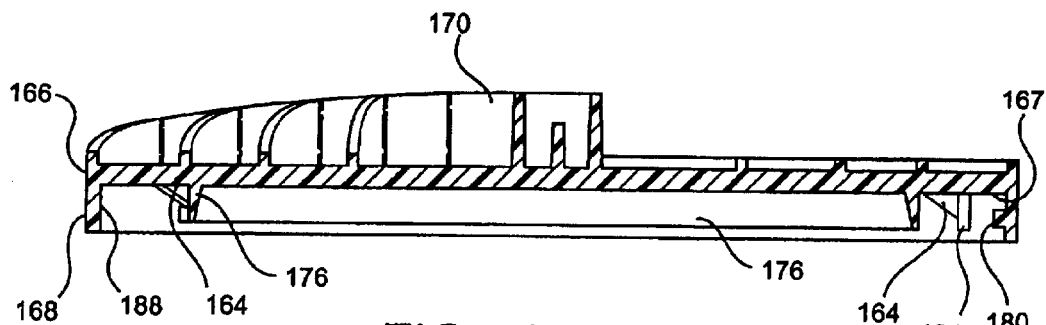
FIG. 17 is a cross sectional side view of the cover of FIG. 12.
Figure 18:
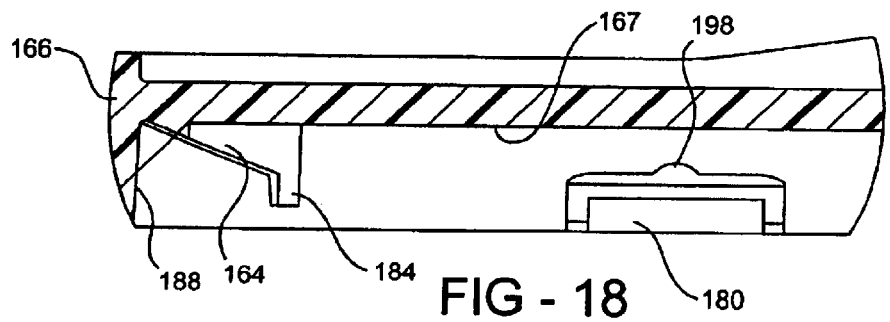
FIG. 18 is an enlarged fragmentary cross sectional view of the cover of FIG. 12.

In the embodiment of FIGS. 12 through 19B, a second locking device 180 is disposed on the cover 166 wherein the first 162 and second 180 locking devices interlock the cover 166 to the base 132 when the cover 166 is mounted to the base 132 and release the cover 166 from the base 132 as the cover 166 is being removed from the base 132. As best shown in FIGS. 16 through 19B, the second locking device 180 is defined as a second tab 180 being supported by the flange 188 and frictionally engaging the first tab 162 when the cover 166 is interlocked to the base 132. The second tab 180 of the cover 166 includes a raised portion 198 which engages the first tab 162 of the base 132 to assists in the mounting and removal of the cover 166 to the base 132. As best shown in FIGS. 17 and 18, the second tab 180 is spaced from a main body portion 167 of the cover 166 to create a gap between the second tab 180 and the cover 166. The first tab 162 becomes wedged between the main body portion 167 of the cover 166 and the second tab 180 within the gap when the cover 166 is mounted to the base 132.

The cover 166 further includes a lifting mechanism 164 disposed adjacent the flange 188 for automatically lifting the cover 166 relative to the base 132 during a removal of the cover 166. In the embodiment of FIGS. 12 through 19B, the lifting mechanism 164 is defined as an angled step 164 mounted to the cover 166 engaging the first tab 162 of the base 132. Preferably, there are three second tabs 180 and three angled steps 164 on the cover 166. The engagement of the first tab 162 with the angled step 164 provides a controlled lifting feature of the cover 166 relative to the base 132 during removal of the cover 166 from the base 132.

A stop mechanism 184 is disposed on the cover 166 to limit a rotatable movement of the cover 166 relative to the base 132. In the embodiment of FIGS. 12 through 19B, the stop mechanism 184 is defined as an appendage 184 extending from the lifting mechanism 164 on the cover 166 whereby the appendage 184 selectively engages the first tab 162 of the base 132 during a rotation of the cover 166 relative to the base 132.

The operation of the container assembly 130 of FIGS. 12 through 19B is now discussed in greater detail. During installation of the cover 166 to the base 132, the annular wedge 176 of the cover 166 engages the chamfer 144 on the upper surface 138 of the inner wall 136 and flexes or otherwise deforms to conform to the configuration of the upper surface 138. Hence, the chamfer 144 guides the distal second end of the annular wedge 176 into the mixing chamber 140 as the cover 166 is mounted to the base 132. The flexing of the annular wedge 176 continues until the cover 166 engages the top surface 134 of the base 132. The flange 188 encompasses the first tabs 162 and top portion of the base 132 and the second tabs 180 are seated within the notches 186 of the base 132. In addition, the seal 172, if used, is wedged between the cover 166 and the top surface 134 of the base 132. In this position, the annular wedge 176 of the cover 166 is biased and sealed against the chamfer 144 of the base 132.

Figure 19A:
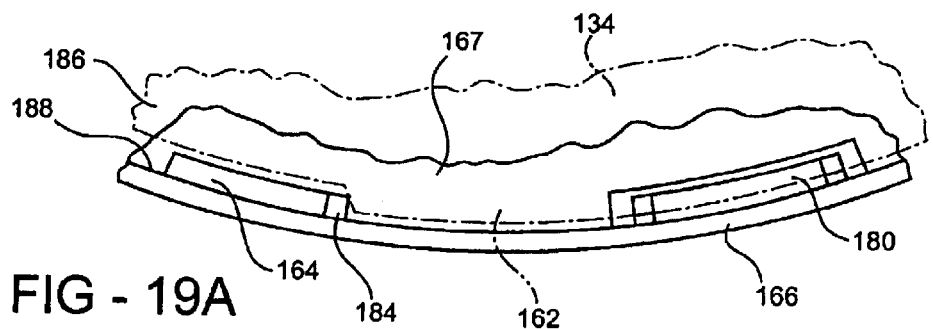
FIG. 19A is an enlarged fragmentary view of the cover of FIG. 12 in a locked position.

The cover 166 is then rotated clockwise relative to the base 132 which moves the second tabs 180 within the notches 186 until second tabs 180 engage the tapered portions 182 of the first tabs 162. The second tabs 180 then move into wedging engagement with the first tabs 162 which further close the cover 166 onto the base 132. In particular, the raised portion 198 of the second tabs 180 engages the first tabs 162. The clockwise rotation continues until the stop tabs 184 engage one of the first tabs 162 as shown in FIG. 19A. The cover 166 is now interlocked and sealed to the base 132 which prevents the powder from escaping from the mixing chamber 140.

Figure 19B:
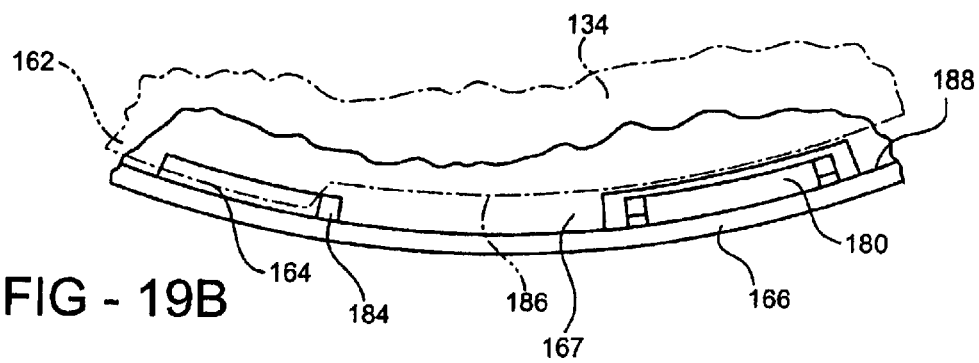
FIG. 19B is an enlarged fragmentary view of the cover of FIG. 12 in a released position.

During removal of the cover 166, a user grasps the handle 170 and rotates the cover 166 counter-clockwise. The second tabs 180 will disengage from the first tabs 162 and the stop tabs 184 will rotate away from the adjacent first tabs 162. In particular, the second tabs 180 will re-align with the notches 186 of the base 132. The angled steps 164 of the cover 166 will then engage the first tabs 162 of the base 132 which automatically lifts the cover 166 relative to the base 132 as the cover 166 is being removed. This controlled lifting of the cover 166 prevents the discharge of material from the mixing chamber 140 by controlling the flexure of the annular wedge 176 against the inner wall 136. The counter-clockwise rotation and lifting of the cover 166 continues until the stop tab 184 again engages the first tabs 162 of the base 132 as shown in FIG. 19B. In this position the annular wedge 176 has returned to the position adjacent the chamfer 144 of the inner wall 136. The annular wedge 176 has little resistance with the inner wall 136 such that the cover 166 can be easily removed from the base 132.

Figure 20:
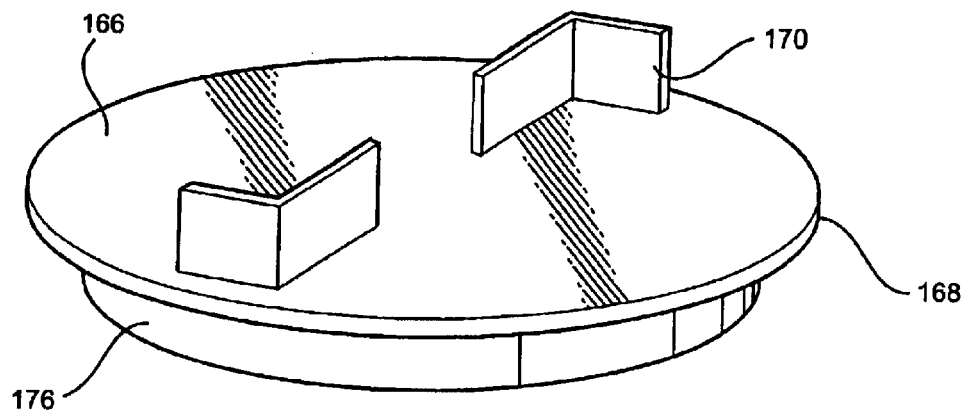
FIG. 20 is a perspective view of another alternative embodiment for the cover.
Figure 21:
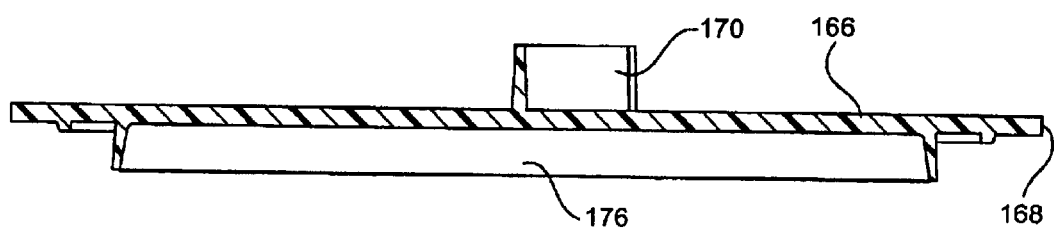
FIG. 21 is a side view of the alternative cover of FIG. 20.

Turning to FIGS. 20 and 21, yet another alternative embodiment of the cover 166 is shown. This embodiment of the cover 166 does not include an outer flange or a locking device. A sealing portion 176 in accordance with the subject invention extends from the cover 166 and is spaced inwardly from an outer periphery 168.

Obviously, many modifications and variations of the present invention are possible in light of the above teachings such that the invention may be practiced otherwise than as specifically described within the scope of the appended claims.

What is claimed is:

1. A container assembly for mixing materials comprising:
a base having a top surface and an inner wall with said inner wall defining an upper surface and a mixing chamber for mixing the materials with said upper surface including a chamfer angling inwardly from said top surface toward said inner wall;
a cover having an outer periphery and being selectively mounted to said base covering said mixing chamber and being removable from said base exposing said mixing chamber; and
a sealing portion spaced inwardly from said outer periphery and depending from said cover to a distal end with said sealing portion engaging said upper surface of said inner wall when said cover is mounted to said base;
said sealing portion being at least partially flexible and angled outwardly toward said outer periphery such that during said engagement of said sealing portion with said upper surface, said chamfer guides said distal end of said sealing portion into said mixing chamber and said sealing portion flexes and conforms to said upper surface to seal said mixing chamber for preventing an escape of material from said mixing chamber.

2. An assembly as set forth in claim 1 wherein said sealing portion is angled outwardly toward said outer periphery from 0.5 to 20 degrees.

3. An assembly as set forth in claim 1 wherein said sealing portion is further defined as an annular wedge having a first end and a distal second end with said first end being mounted to said cover and being thicker than said distal end when viewed in cross section to at least partially provide said flexibility of said sealing portion.

4. An assembly as set forth in claim 3 wherein said distal second end includes a beveled section to further provide said flexibility of said sealing portion.

5. An assembly as set forth in claim 3 wherein said chamfer guides said distal second end of said annular wedge into said mixing chamber as said cover is mounted to said base.

6. An assembly as set forth in claim 1 wherein said sealing portion is integrally formed with said cover.

7. An assembly as set forth in claim 6 wherein said cover and sealing portion are integrally formed of a polymeric material.

8. An assembly as set forth in claim 1 wherein said cover is seated upon said top surface when said cover is mounted to said base.

9. An assembly as set forth in claim 8 wherein said top surface extends substantially transverse to said inner wall and said base further includes an outer ridge extending upwardly from said top surface substantially parallel with said upper surface of said inner wall whereby said ridge surrounds said outer periphery of said cover when said cover is mounted to said base.

10. An assembly as set forth in claim 8 wherein said top surface extends substantially transverse to said inner wall and said cover further includes an outer flange substantially encapsulating said top surface when said cover is mounted to said base.

11. An assembly as set forth in claim 8 wherein said top surface includes at least one aperture for evacuating gases from said mixing chamber.

12. An assembly as set forth in claim 8 further including a seal disposed between said cover and said top surface of said base when said cover is mounted to said base.

13. An assembly as set forth in claim 8 further including a first locking device disposed on said top surface of said base.

14. An assembly as set forth in claim 13 further including a second locking device disposed on said outer periphery of said cover wherein said first and second locking devices interlock said cover to said base when said cover is mounted to said base and release said cover from said base as said cover is being removed from said base.

15. An assembly as set forth in claim 14 further including a lifting mechanism disposed on at least one of said base and cover for automatically lifting said cover relative to said base as said cover is being removed from said base for preventing a discharge of material from said mixing chamber.

16. An assembly as set forth in claim 15 wherein said first locking device is further defined as a first tab extending substantially parallel to said top surface.

17. An assembly as set forth in claim 16 wherein said second locking device is further defined as a second tab extending from said outer periphery of said cover and frictionally engaging said first tab when said cover is interlocked to said base.

18. An assembly as set forth in claim 17 wherein said lifting mechanism is further defined as an angled step engaging one of said first and second tabs to lift said cover during said removal of said cover from said base.

19. An assembly as set forth in claim 1 further including a mixing device mountable to said base for mixing the material in said mixing chamber when said cover is removed from said base.

20. An assembly as set forth in claim 1 wherein said base includes a bottom opening and further including a piston disposed within said bottom opening.

21. An assembly as set forth in claim 20 wherein said piston includes an annular ring abutting said bottom opening to seal said mixing chamber and prevent an escape of material from said mixing chamber.

22. A container assembly for mixing materials comprising:
a base having a top surface and an inner wall with said inner wall defining a mixing chamber for mixing the materials;

a first locking device disposed on said top surface of said base;

a cover having an outer periphery and being selectively mounted to said base covering said mixing chamber and being removable from said base exposing said mixing chamber;

a second locking device disposed adjacent said outer periphery of said cover wherein said first and second locking devices interlock said cover to said base when said cover is mounted to said base and release said cover from said base as said cover is being removed from said base; and a lifting mechanism disposed on at least one of said base and cover for automatically lifting said cover relative to said base as said cover is being removed from said base for preventing a discharge of material from said mixing chamber.

23. An assembly as set forth in claim 22 wherein said top surface extends substantially transverse to said inner wall with said cover being seated upon said top surface when said cover is mounted to said base.

24. An assembly as set forth in claim 23 wherein said first locking device is further defined as a first tab extending substantially parallel to said top surface.

25. An assembly as set forth in claim 24 wherein said second locking device is further defined as a second tab extending from said outer periphery of said cover and frictionally engaging said first tab when said cover is interlocked to said base.

26. An assembly as set forth in claim 25 wherein at least one of said first and second tabs include a tapered portion.

27. An assembly as set forth in claim 26 wherein said second tab of said cover includes said tapered portion.

28. An assembly as set forth in claim 27 wherein said base further includes an outer ridge extending upwardly from said top surface substantially parallel with said inner wall whereby said ridge surrounds said outer periphery of said cover when said cover is mounted to said base.

29. An assembly as set forth in claim 28 wherein said first tab extends from said ridge toward said inner wall.

30. An assembly as set forth in claim 29 wherein said top surface includes an aperture disposed below said first tab for evacuating gases from said mixing chamber.

31. An assembly as set forth in claim 26 wherein said first tab of said base includes said tapered portion.

32. An assembly as set forth in claim 31 wherein said cover further includes an outer flange substantially encapsulating said top surface when said cover is mounted to said base with said flange supporting said second tab.

33. An assembly as set forth in claim 32 wherein said top surface includes an aperture for evacuating gases from said mixing chamber.

34. An assembly as set forth in claim 26 further including a stop mechanism disposed on said cover to limit a rotatable movement of said cover relative to said base.

35. An assembly as set forth in claim 34 wherein said stop mechanism is defined as a stop tab extending from said cover whereby said stop tab selectively engages said first tab of said base during a rotation of said cover relative to said base.

36. An assembly as set forth in claim 34 wherein said stop mechanism is defined as an appendage extending from said lift mechanism on said cover whereby said appendage selectively engages said first tab of said base during a rotation of said cover relative to said base.

37. An assembly as set forth in claim 22 wherein said base includes a bottom opening and further including a piston disposed within said bottom opening.

38. An assembly as set forth in claim 37 wherein said piston includes an annular ring abutting said bottom opening to seal said mixing chamber and prevent an escape of material from said mixing chamber.

39. An assembly as set forth in claim 22 wherein said lifting mechanism is further defined as an angled step engaging one of said first and second tabs to lift said cover during said removal of said cover from said base.

40. An assembly as set forth in claim 39 wherein said angled step is mounted to said top surface of said base and engages said second locking device of said cover.

41. An assembly as set forth in claim 39 wherein said angled step is mounted to said cover and engages said first tab of said base.

42. An assembly as set forth in claim 22 further including a seal disposed between said cover and said top surface of said base when said cover is mounted to said base.

43. An assembly as set forth in claim 22 further including a mixing device mountable to said base for mixing the material in said mixing chamber when said cover is removed from said base.

44. An assembly as set forth in claim 22 further including a sealing portion depending from said cover and engaging said upper surface of said inner wall when said cover is mounted to said base.

45. An assembly as set forth in claim 44 wherein said sealing portion is at least partially flexible and angled outwardly toward said outer periphery such that during said engagement of said sealing portion with said upper surface, said sealing portion flexes and conforms to said upper surface to seal said mixing chamber.

46. An assembly as set forth in claim 45 wherein said sealing portion is spaced inwardly from said outer periphery.

47. An assembly as set forth in claim 46 wherein said sealing portion is further defined as an annular wedge having a first end and a distal second end with said first end being mounted to said cover and being thicker than said distal end when viewed in cross section to at least partially provide said flexibility of said sealing portion.

48. An assembly as set forth in claim 47 wherein said distal second end includes a beveled section to further provide said flexibility of said sealing portion.

49. An assembly as set forth in claim 48 wherein said upper surface of said inner wall includes a chamfer such that said chamfer guides said distal second end of said annular wedge into said mixing chamber as said cover is mounted to said base.

50. A container assembly for mixing materials comprising:

a base having an inner wall defining an upper surface and a mixing chamber for mixing the materials;

a cover having an outer periphery and being selectively mounted to said base covering said mixing chamber and being removable from said base exposing said mixing chamber;

a sealing portion depending from said cover and engaging said upper surface of said inner wall when said cover is mounted to said base;

said sealing portion being at least partially flexible and angled outwardly toward said outer periphery such that during said engagement of said sealing portion with said upper surface, said sealing portion flexes and conforms to said upper surface to seal said mixing chamber for preventing an escape of material from said mixing chamber; and a mixing device mountable to said base for mixing the material in said mixing chamber when said cover is removed from said base.

51. An assembly as set forth in claim 50 wherein said sealing portion is further defined as an annular wedge having a first end and a distal second end with said first end being mounted to said cover and being thicker than said distal end when viewed in cross section to at least partially provide said flexibility of said sealing portion.

52. An assembly as set forth in claim 51 wherein said upper surface of said inner wall includes a chamfer such that said chamfer guides said distal second end of said annular wedge into said mixing chamber as said cover is mounted to said base.

53. An assembly as set forth in claim 50 wherein said base further includes a top surface with said cover being seated upon said top surface when said cover is mounted to said base.

54. An assembly as set forth in claim 53 wherein said top surface extends substantially transverse to said inner wall and said base further includes an outer ridge extending upwardly from said top surface substantially parallel with said upper surface of said inner wall whereby said ridge surrounds said outer periphery of said cover when said cover is mounted to said base.

55. An assembly as set forth in claim 53 wherein said top surface extends substantially transverse to said inner wall and said cover further includes an outer flange substantially encapsulating said top surface when said cover is mounted to said base.

56. An assembly as set forth in claim 53 wherein said top surface includes at least one aperture for evacuating gases from said mixing chamber.

57. An assembly as set forth in claim 53 further including a first locking device disposed on said top surface of said base.

58. An assembly as set forth in claim 57 further including a second locking device disposed on said outer periphery of said cover wherein said first and second locking devices interlock said cover to said base when said cover is mounted to said base and release said cover from said base as said cover is being removed from said base.

59. An assembly as set forth in claim 58 further including a lifting mechanism disposed on at least one of said base and cover for automatically lifting said cover relative to said base as said cover is being removed from said base for preventing a discharge of material from said mixing chamber.

* * * * *